US012782052B2

(12) United States Patent
Schroeder

(10) Patent No.: US 12,782,052 B2
(45) Date of Patent: Nov. 3, 2026

(54) ADAPTER FOR CONNECTING AN ENDOSCOPE WITH AN AIR SUPPLY CONNECTOR OF A STORAGE CABINET, STORAGE CABINET, ENDOSCOPE STORAGE SYSTEM AND METHODS FOR CONNECTING AND DISCONNECTING AN ADAPTER TO A STORAGE CABINET

(71) Applicant: OLYMPUS Winter & Ibe GmbH, Hamburg (DE)

(72) Inventor: Stefan Schroeder, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 669 days.

(21) Appl. No.: 18/225,785

(22) Filed: Jul. 25, 2023

(65) Prior Publication Data

US 2024/0183612 A1 Jun. 6, 2024

Related U.S. Application Data

(60) Provisional application No. 63/429,251, filed on Dec. 1, 2022.

(51) Int. Cl.

| | |
|---|---|
| ***A61B 50/10*** | (2016.01) |
| ***A61B 50/13*** | (2016.01) |
| ***F26B 21/00*** | (2026.01) |
| ***F26B 21/20*** | (2026.01) |
| ***F26B 21/50*** | (2026.01) |
| ***F26B 25/16*** | (2006.01) |

(52) U.S. Cl.

CPC .............. *F26B 21/50* (2026.01); *A61B 50/10* (2016.02); *F26B 25/16* (2013.01); *A61B 2050/105* (2016.02)

(58) Field of Classification Search

CPC ........ F26B 21/50; F26B 21/006; F26B 21/20; F26B 21/208; F26B 25/06; A61B 50/10; A61B 50/13; A61B 2050/105; A61B 90/70

USPC ............. 134/166 R, 200, 170, 169 C, 166 C; 15/300

See application file for complete search history.

(56) References Cited

U.S. PATENT DOCUMENTS 6,485,684 B1 * 11/2002 Mapson ............. A61B 1/00057 206/370
10,413,382 B2 9/2019 Smart
10,463,441 B2 11/2019 Tate et al.
2008/0294008 A1 * 11/2008 Toyama ................. A61B 1/015 600/156

(Continued)

FOREIGN PATENT DOCUMENTS

DE 10 2009 022 502 A1 12/2010

*Primary Examiner* — Deming Wan

(74) *Attorney, Agent, or Firm* — Scully, Scott, Murphy & Presser, P.C.

(57) ABSTRACT

An adapter including: an air inlet connector configured to be connected to an air supply connector of a storage cabinet; at least one endoscope connector configured to be connected to an endoscope port of an endoscope; and at least one tube connecting the air inlet connector and the at least one endoscope connector. Wherein the adapter comprises a RFID tag, the RFID tag is configured to store adapter type information about an adapter type of the adapter, and the RFID tag is configured to send the adapter type information to a RFID receiver of the storage cabinet.

14 Claims, 5 Drawing Sheets

(56) References Cited

U.S. PATENT DOCUMENTS

| | | | | |
|---|---|---|---|---|
| 2011/0097248 | A1* | 4/2011 | Tomita | A61B 1/00059 422/292 |
| 2015/0216608 | A1 | 8/2015 | Eschborn et al. | |
| 2019/0175296 | A1 | 6/2019 | Tate et al. | |
| 2019/0333420 | A1* | 10/2019 | Danielson | F16L 37/20 |
| 2020/0118674 | A1* | 4/2020 | Le | A61B 1/121 |

* cited by examiner

ADAPTER FOR CONNECTING AN ENDOSCOPE WITH AN AIR SUPPLY CONNECTOR OF A STORAGE CABINET, STORAGE CABINET, ENDOSCOPE STORAGE SYSTEM AND METHODS FOR CONNECTING AND DISCONNECTING AN ADAPTER TO A STORAGE CABINET

CROSS-REFERENCE TO RELATED APPLICATION

The present application is based upon and claims the benefit of priority from U.S. Provisional Application No. 63/429,251 filed on Dec. 1, 2022, the entire contents of which is incorporated herein by reference.

BACKGROUND

Field

The present disclosure relates to an adapter for connecting an endoscope with an air supply connector of a storage cabinet. The present disclosure further relates to a storage cabinet, an endoscope storage system, a method for connecting an adapter to a storage cabinet and a method of disconnecting an adapter from a storage cabinet.

Prior Art

Storage cabinets are often used to store and dry endoscopes after they have been cleaned and disinfected. In order to dry the inside of the endoscope and protect them from contamination, an airflow is guided through the endoscope channels during storage. This requires an adapter connecting ports of the endoscope with an air supply connector of the storage cabinet.

However, as different types of endoscopes comprise different types and numbers of endoscope ports, each endoscope type requires a specific adapter. These adapters differ from each other in their geometry and design as well as in the flow parameters required for the airflow going through the adapters. When storing an endoscope in the storage cabinet, a user must select the correct adapter for this type of endoscope. Then, after connecting the endoscope to the cabinet with the adapter, the user has to select the correct flow parameters for this adapter. These steps are prone to mistakes. For example, the user may select the wrong type of adapter or select incorrect flow parameters. Such mistakes can result in the contamination of the endoscope, which poses a great danger for patients during surgery.

SUMMARY

An object is to improve handling and safety when using adapters to connect an endoscope with an air supply connector of a storage cabinet.

Such object can be solved by an adapter for connecting an endoscope with an air supply connector of a storage cabinet, wherein the adapter comprises an air inlet connector configured to be connected to the air supply connector of the storage cabinet, at least one endoscope connector configured to be connected to an endoscope port of the endoscope and at least one tube connecting the air inlet connector and the at least one endoscope connector, wherein the adapter further comprises a RFID tag, wherein the RFID tag stores adapter type information about an adapter type of the adapter, wherein the RFID tag is configured to send the adapter type information to a RFID receiver of the storage cabinet.

The adapter utilizes the RFID tag to transmit the adapter type information to the storage cabinet, so that the adapter type information are available in the storage cabinet. Thus, the storage cabinet can identify a type of the adapter and a mix-up of adapters is prevented. The adapter type information can be stored in a storage device of the RFID tag.

The RFID tag can be arranged on or inside the air inlet connector. The air inlet connector is well suited to receive the RFID tag, because the air inlet connector is brought in close contact with the storage cabinet when connecting the air inlet connector to the air supply connector of the storage cabinet. In addition, the air inlet connector configuration is very similar or identical in every adapter to allow the connection with the air supply connector. Thus, the RFID tag can be arranged in or on every adapter in the same way.

The adapter type information can comprise flow parameters, wherein the flow parameters can specify an air pressure value and/or a flow rate value of a pressurized air flow to be guided through the adapter.

By including the flow parameters in the adapter type information, the flow parameters automatically become available in the storage cabinet without the need for a user input. In this way, the storage cabinet can automatically adapt the pressurized airflow to the adapter specifications. Thus, a mistake in selecting the flow parameters can be prevented.

According to further embodiments, the adapter type information can comprise one or more than one parameter selected from the following list:

- a connection time for a user to connect the endoscope adapter and the
- a minimum and/or a maximum valve opening position of the air valve in at least one of the air supply connectors of the storage cabinet, wherein the air supply connector comprises the air valve, which is configured to control the pressurized air flow through the air supply connector, such as during a main drying phase,
- a minimum and/or a maximum pressure of the pressurized air flow through the air supply connector, such as during a main drying phase,
- a duration of a pre-drying phase,
- an airflow and/or an air flow pulse length during a pre-drying phase,
- a duration of a storage phase, and
- an airflow and/or a pulse length during a storage phase.

A storage cabinet configured to apply an air pressure to the air supply connectors in the an air stream can be provided, which can be suitable for drying of a surgical instrument having an internal channel, such as an endoscope. The pressure can be applied such that the drying of the surgical instrument can be performed in different phases. For example, there is a pre-drying phase, a subsequent main drying phase and a subsequent storage phase. During the pre-drying phase, the internal channel of the surgical instrument is pre-dried. The drying of the internal channel is performed during the main drying phase. During the storage phase, the surgical instrument is stored for later use.

The above parameters can be important for safely drying of surgical instruments having an internal channel, such as endoscopes having a flexible shaft.

The minimum and the maximum valve opening position can be defined in % of the maximum open position. The minimum and the maximum pressure can be defined in units of millibar (mbar). The length of the pre-drying phase and the main drying phase can be defined in minutes (min) and the airflow can be defined in liters per minute (l/min). The pulse length can be defined in seconds (s).

Such object can also be solved by a storage cabinet comprising an air supply, at least two air supply connectors connected to the air supply, at least one RFID receiver and a control device (i.e., a controller comprising hardware), wherein the at least two air supply connectors are configured to be connected to the air inlet connector of the adapter according to one of the previous embodiments, wherein the air supply can be configured to apply an air pressure to the air supply connectors, wherein the air supply connectors can each comprise an air valve, wherein the air valve in each air supply connector can be configured to be mechanically opened when a connection is established between the air inlet connector of the adapter and the air supply connector comprising this air valve, wherein the opening of the air valve can cause a pressurized air flow through the air supply connector comprising the opened air valve to the adapter, wherein the control device can be configured to detect the pressurized air flow in order to detect which air supply connector has been connected to the air inlet connector, wherein the at least one RFID receiver can be configured to receive the adapter type information from the RFID tag of the adapter and to transmit the adapter type information to the control device, wherein the control device can be configured to adapt flow parameters of the pressurized air flow based on the adapter type information.

The storage cabinet can be utilized for storing and drying endoscopes. For this purpose, the storage cabinet can comprise a number of holders, configured to hold the endoscope in the storage cabinet in a hanging position. The endoscope ports of the endoscope can be connected to the endoscope connectors of the adapter and the air inlet connector of the adapter can be connected to the air supply connector of the storage cabinet. When connecting the air inlet connector of the adapter to the air supply connector in this way, the air valve of this air supply connector is opened mechanically. Due to the air pressure generated by the air supply, the opening of the valve results in the pressurized air flow flowing from the air supply connector through the tube of the adapter to the endoscope. The control device recognizes the pressurized air flow and thus learns which air supply connector has been connected to the adapter. Based on the adapter type information received from the RFID tag of the adapter, the control device can then regulate for example the pressurized air flow. For example, the control device can control the air supply in order to increase and/or decrease a flow rate value and/or an air pressure value of the pressurized air flow, so that these values match the specifications of the adapter currently connected to the air supply connector. The flow parameters can be selected automatically by the control device based on the information contained in the adapter itself. This can prevent a mix-up of adapters and an erroneous selection of flow parameters by the user.

The air flow and the air pressure are important parameters. However, also the time length for drying and the storage phase can be important and hence, further parameters can be part of the information received from the RFID tag. The storage cabinet can receive a set of parameters or a selection of parameters. The parameters can be selected from the list of parameters, which is mentioned in connection with the adapter type information above. Different endoscope types can require different lengths of drying time and may have different maximum storage times. This can be reflected in one or more of the mentioned parameters.

The control device can be configured to detect the pressurized air flow with a sensor. The sensor can be arranged inside the air supply connector or in a supply line between the air supply and the air supply connector. The air pressure applied to the air supply connectors can result in a minimal air flow when the air valves are opened. This minimal airflow does not require a high flow rate or high air pressure, because its main purpose is to allow the control device to detect the connection between the air inlet connector and the air supply connector. After this connection has been detected, the pressure and/or flow rate can be increased to the values required by the adapter.

The control device, also known as a controller or a control unit, may be a computer, a circuit board or a similar device for controlling the functions of the storage cabinet. The control device and/or the air supply can be configured to set different flow parameters for each of the air supply connectors. This enables a user to place different types of endoscopes in the storage cabinet and still apply the correct air flow parameters to each endoscope.

The storage cabinet can comprise at least two RFID receivers, wherein one of the at least two RFID receivers can be arranged on or inside each of the at least two air supply connectors. Thus, the at least one RFID receiver can comprises at least two RFID receivers. In other words, each of the air supply connectors can comprise a designated RFID receiver. This setup places the RFID receivers in close proximity to the RFID tags of the adapter, when the adapter is connected to the air supply connector. This enables the adapter type information to be reliably transmitted to the storage cabinet without any additional steps. In addition, it is ensured, that the adapter type information are always transmitted when connecting the adapter to the storage cabinet, so that the adapter type information are available to the control device. Also, it can be ensured, that the adaptor type information transmitted from the RFID tag actually match the type of adapter connected to the air supply connector. Especially when handling multiple endoscopes at the same time, this setup prevents the RFID tag from a first adapter is scanned but then a different, second adapter is connected to the storage cabinet.

According to another embodiment, one of the at least one RFID receivers can be arranged as part of a control panel of the storage cabinet. This arrangement of the RFID receiver only requires a single RFID receiver, which is always readily accessible to a user.

According to yet another embodiment, one of the at least one RFID receivers can be arranged as part of a control panel of the storage cabinet. The arrangement as part of the control panel can be utilized since the user usually has to access the control panel anyway, so that no additional step has to be taken in order to transmit the adapter type information. In addition, only one RFID receiver can be required.

The control device can be configured to adapt flow parameters of the pressurized air flow of each air supply connector only after the connection of this air supply connector to the air inlet connector has been detected. By adapting the flow parameters only after the connection has been detected, mistakes in the handling of the adapter can be prevented. According to a further embodiment, each air supply connector can comprise a designated RFID receiver, wherein the RFID receiver and/or the control device can be configured to receive and/or process the adapter type information only after the connection of the air supply connector to the air inlet connector has been detected. This can prevent a mix-up of adapters, as it is made sure that the adapter type information are transmitted after the connection has been made. Thus, the connection of an adapter not matching the previously transmitted adapter type information can be prevented.

The control device can be configured to measure a connection time for which the adapter is connected to one of the air supply connectors, compare the connection time with a predefined lifetime of the adapter and generate a warning when the connection time exceeds the lifetime. The measurement of the connection time allows a user to track the usage of the adapter. The warning is, for example, displayed in the control panel of the storage cabinet and/or the warning may be communicated as an acoustic warning message. The warning may include individual maintenance suggestions.

Such object can be further solved by an endoscope storage system comprising at least one adapter according to any of the previously mentioned embodiments and a storage cabinet according to one of the previously mentioned embodiments.

The same or similar advantages apply to the endoscope storage system as previously mentioned with respect to the adapter and the storage cabinet.

Such object can be further solved by a method for connecting an adapter, such as any of the previously mentioned embodiments, to one of at least two air supply connectors of a storage cabinet, such as according to one of the previously mentioned embodiments, comprising the following steps:

- transmitting adapter type information from a RFID tag of the adapter to a RFID receiver of the storage cabinet,
- connecting an air inlet connector of the adapter to a first air supply connector of the at least two air supply connectors, wherein an air pressure is applied to all air supply connectors with an air supply of the storage cabinet, wherein an air valve in the first air supply connector is opened by connecting the air inlet connector to the first air supply connector, wherein the opening of the air valve causes a pressurized air flow through the first air supply connector to the adapter,
- detecting, with a control device of the storage cabinet, which of the at least two air supply connectors has been connected with the air inlet connector by detecting the pressurized air flow,
- sending the adapter type information from the RFID receiver to the control device, and
- adapting flow parameters of the pressurized air flow based on the adapter type information.

This method can ensure that the flow parameters are adapted automatically according to the specifications of the adapter. The control device can also analyze the adaptor type information to determine an adapter type of the adapter. This can further reduce the chance of a mix-up of adapters.

According to an embodiment, before the previously mentioned steps, a user RFID tag carried by a user can transmit user data to the RFID receiver of the storage cabinet. The control device can receive the user data from the RFID receiver and analyze if the user corresponding to the user data has access to the storage cabinet. A door to the storage cabinet can be unlocked only if the user has access to the storage cabinet.

The step of adapting the flow parameters can be performed after the step of detecting which of the at least two air supply connectors has been connected with the air inlet connector.

A connection time, for which the adapter is connected to one of the air supply connectors, can be measured, wherein the connection time is compared with a predefined lifetime of the adapter, wherein a warning is generated when the connection time exceeds the lifetime.

According to an embodiment, the method comprises the step of connecting at least one endoscope connector of the adapter to at least one endoscope port of an endoscope. The endoscope can be arranged in a holder of the storage cabinet. The endoscope can comprise an endoscope RFID tag configured to transmit endoscope information to the storage cabinet. Transmitting the endoscope information from the endoscope RFID tag to the storage cabinet enables the control device of the storage cabinet to identify the endoscope and/or an endoscope type of the endoscope. When both the endoscope information and the adapter type information are made available to the control device, the control device may check if the endoscope is connected to a fitting adapter.

Such object can be further solved by a method for disconnecting an adapter, such as according to any of the previously mentioned embodiments, from a first air supply connector of at least two air supply connectors of a storage cabinet, such as according to any of the previously mentioned embodiments, comprising the following steps:

- disconnecting an air inlet connector of the adapter from the first air supply connector, wherein an air valve in the first air supply connector can be closed by disconnecting the air inlet connector from the first air supply connector, wherein the closing of the air valve can cause a pressurized air flow through the first air supply connector to stop,
- detecting, with a control device of the storage cabinet, which of the at least two air supply connectors has been disconnected from the air inlet connector by detecting the termination of the pressurized air flow,
- setting flow parameters for an air pressure applied to the first air supply connector back to a predefined value.

The same or similar advantages apply to the method for connecting an adapter and the method for disconnecting an adapter as previously mentioned with respect to the adapter, the storage cabinet and the endoscope storage system.

The predefined value for the air pressure can be chosen to be a minimal value. When connecting the air inlet connector to the first air supply connector, the air pressure of the predefined value can generate a pressurized air flow that is detectable, but low enough to avoid damages to any kind of adapters or endoscopes connected to the air supply connector. The method for disconnecting an adapter can apply to disconnecting the adapter from all air supply connectors of the storage cabinet.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings.

In the drawings, the same or similar types of elements or respectively corresponding parts are provided with the same reference numbers in order to prevent the item from needing to be reintroduced.

DETAILED DESCRIPTION

Figure 1:
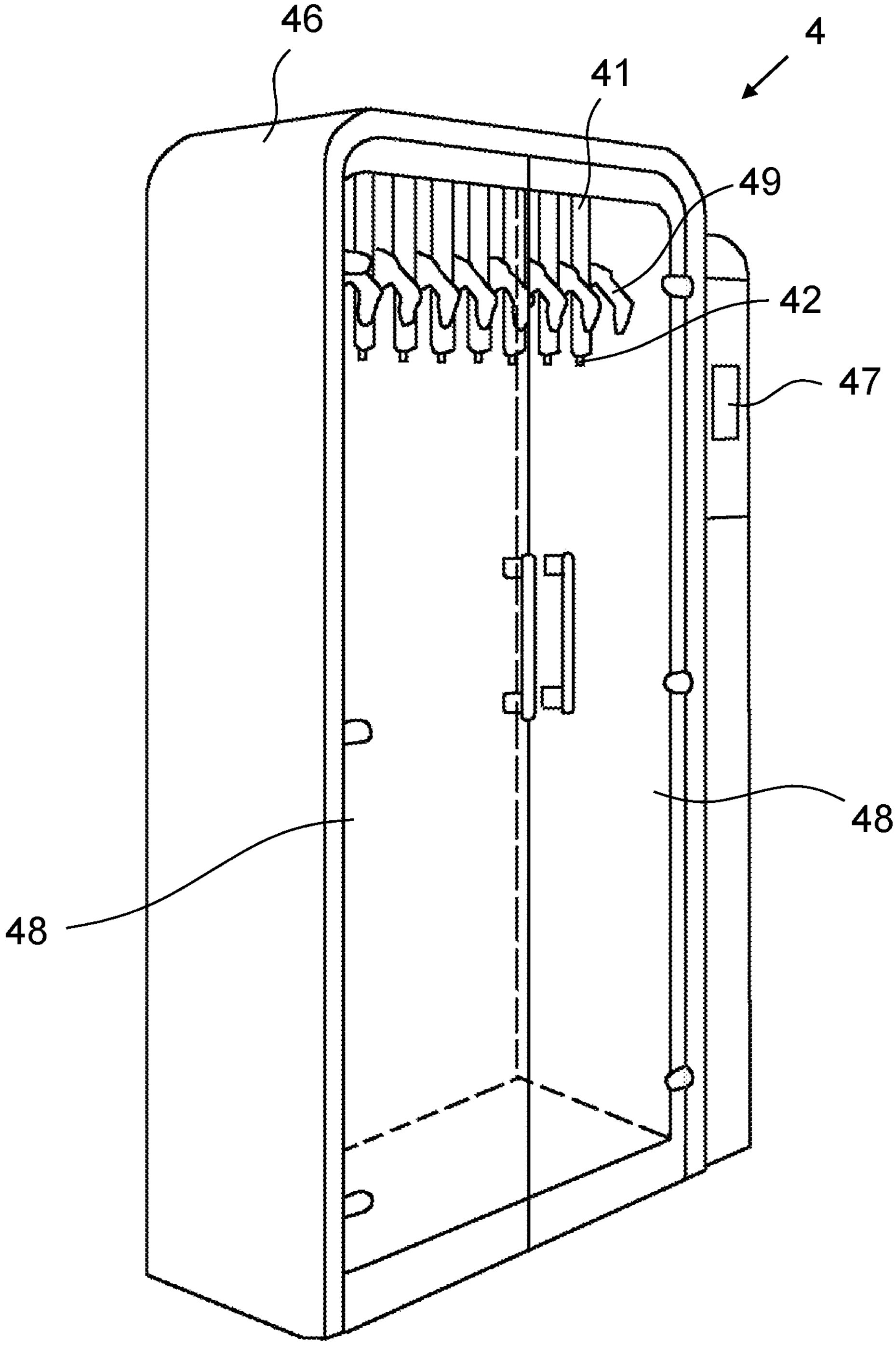
FIG. 1 illustrates a schematic perspective representation of a storage cabinet for storing and drying endoscopes.

FIG. 1 shows a schematic simplified representation of a storage cabinet 4. Such a storage cabinet 4 is used to store and dry endoscopes after they have been cleaned and disinfected. The storage cabinet 4 comprises a hull 46, which encloses a storage space. The storage space can be accessed by opening doors 48. Inside the storage space, the storage cabinet 4 comprises a number of holders 49, which are configured to receive a handle of an endoscope. This allows a user to hang the endoscopes in the storage cabinet 4 by arranging the handles of the endoscopes in the holders 49. The holders 49 are each connected with an air supply connector 41, which are configured to supply pressurized air. The air supply connectors 41 comprise an air valve 42 in order to prevent the pressurized air from escaping the air supply connector 41, as long as no endoscope is connected to the air supply connector 41. In order to increase the clarity of the drawing, only one air supply connector 41, one air valve 42 and one holder 49 have been assigned a reference sign in FIG. 1.

When placing an endoscope in the storage cabinet 4, an adapter has to be used to connect the air supply connector 41 with the endoscope ports of the endoscope. These adapters are specific to the type of the endoscope and differ from each other in their form and geometry as well as in the required flow parameters of the pressurized air flowing through the adapter. This makes it necessary to choose the correct adapter for each endoscope and then select the correct flow parameters, so that the correct air pressure and/or flow rate of pressurized air is applied to the adapter and the endoscope channels. These parameters may be selected on a control panel 47 of the storage cabinet 4. However, a user may mistakenly select wrong flow parameters for an adapter, causing an incorrect drying of the endoscope, which may result in a contamination.

Figure 2:
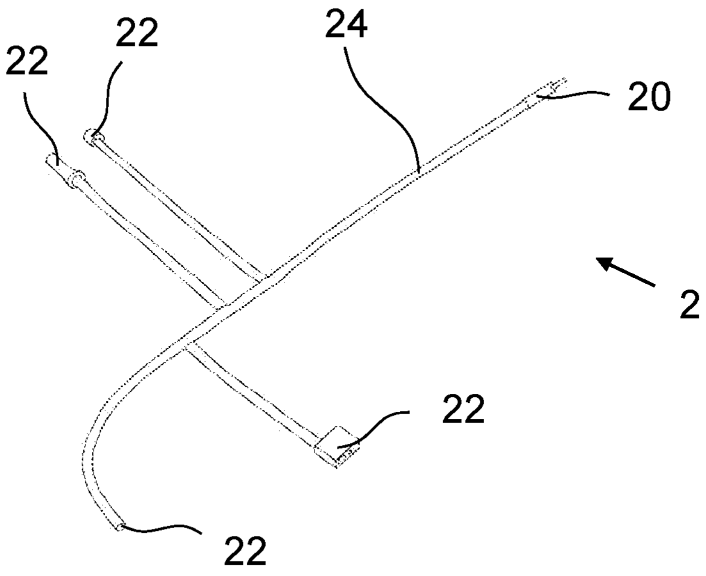
FIG. 2 illustrates a schematic perspective representation of an adapter for connecting an air inlet connector of an adapter to an air supply connector of a storage cabinet.

FIG. 2 shows a schematic simplified representation of an adapter 2 for connecting the endoscope with the air supply connector 41. The adapter 2 comprises an air inlet connector 20, which is configured to be connected to the air supply connector 41. In addition, the adapter 2 comprises a number of endoscope connectors 22, which are configured to be connected to endoscope ports of the endoscope. The endoscope connectors 22 are connected to the air inlet connector 20 by a tube 24, which guides the pressurized air flow from the air inlet connector 20 to the different endoscope connectors 22. The number and arrangement of the endoscope connectors 22 is dependent on the type of adapter. Thus, the adapter 2 may comprise more or less endoscope connectors 22 than shown in FIG. 2 and the endoscope connectors 22 may have a different arrangement.

Figure 3:
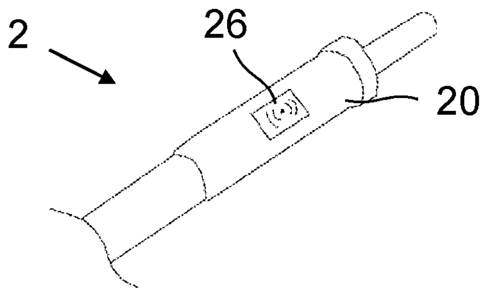
FIG. 3 illustrates a schematic enlarged representation of an air inlet connector of an adapter.

FIG. 3 shows a schematic simplified representation of an embodiment of an adapter 2. This adapter 2 comprises a RFID tag 26 in the air inlet connector 20. In different embodiments, the RFID tag 26 may be arranged on or in the tube 24 or the endoscope connectors 22. The RFID tag 26 stores adapter type information specific to the adapter 2. For example, the adapter type information specify the type of adapter 2 and the flow parameters of the pressurized air required for this adapter 2.

Figure 4:
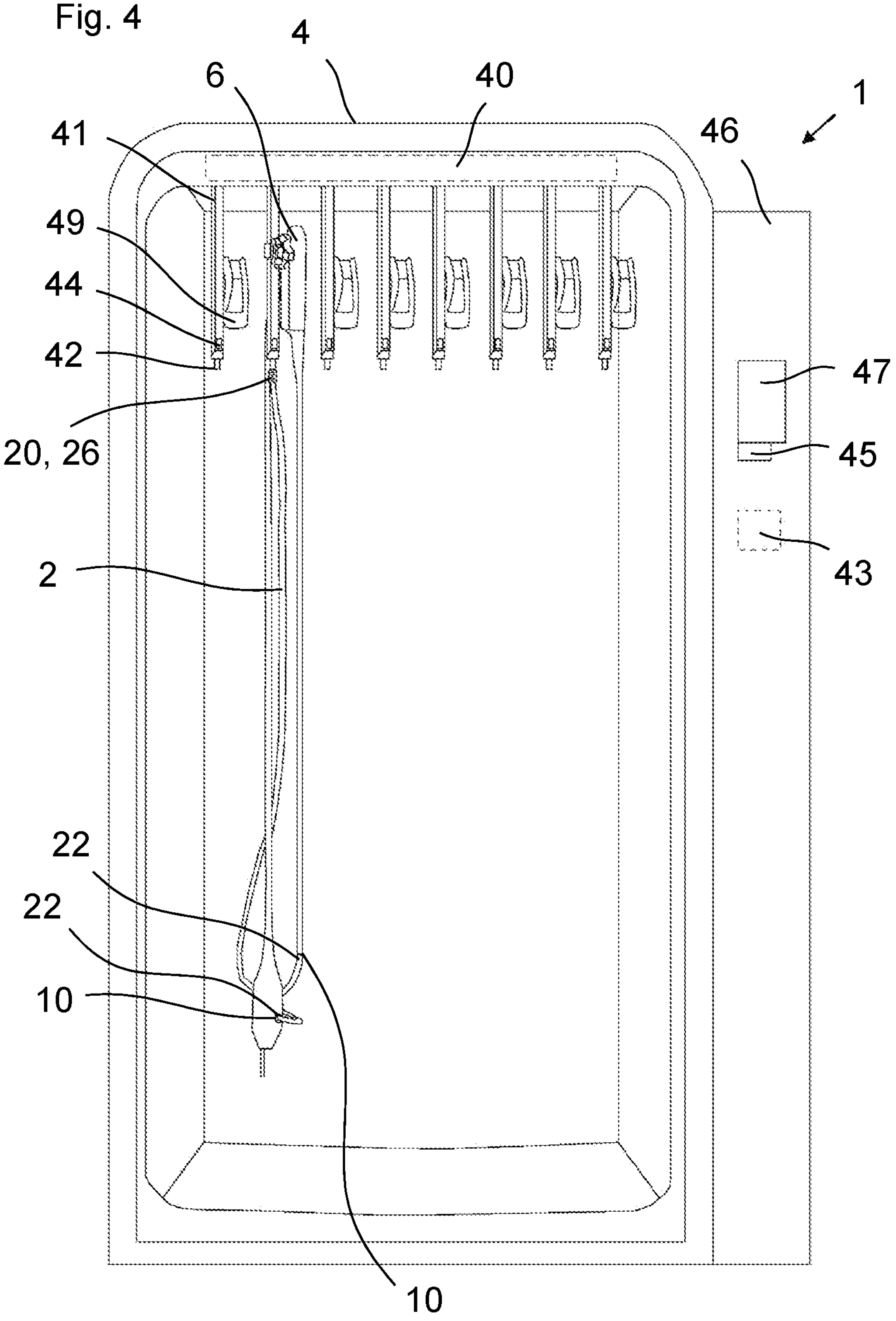
FIG. 4 illustrates a schematic simplified representation of a storage cabinet with an endoscope and an adapter.

FIG. 4 shows a schematic simplified representation of an endoscope storage system 1 comprising a storage cabinet 4 and at least one adapter 2. For better visibility, the doors 48 of the storage cabinet 4 are omitted in FIG. 4. An endoscope 6 is arranged in the storage cabinet 4 and connected to one of the air supply connectors 41 with the adapter 2. The storage cabinet 4 comprises a control device (controller) 43, which is connected to an air supply 40. As both the control device 43 and the air supply 40 are arranged inside the hull 46 and would thus not be visible in FIG. 4, they are represented with dashed lines. The air supply 40 is connected to all of the air supply connectors 41 and applies an air pressure to the air supply connectors 41. The air valves 42 arranged in each air supply connector 41 prevent the air pressure from resulting in an airflow, as long as no adapter 2 is connected to the air supply connector 41.

The storage cabinet 4 in the embodiment shown in FIG. 4 further comprises RFID receivers 44 in each of the air supply connectors 41 and an RFID receiver 45 arranged on the hull 46 as part of the control panel 47. The RFID receivers 44, 45 are configured to receive the adapter type information from the RFID tag 26 of the adapter 2. In this way, the adapter type information is directly sent from the adapter 2 to the storage cabinet 4 without the need of a manual input by a user. In order to transmit the adapter type information, the RFID tag 26 may be held close to the RFID receiver 45 by a user, before the user connects the adapter 2 to the air supply connector 41. The adapter type information may also be transmitted when the air inlet connector 20 of the adapter 2 is connected to the air supply connector 41, as shown in FIG. 4. When this connection is made, the RFID tag 26 arranged in the air inlet connector 20 is in close proximity to the RFID receiver 44 arranged in the air supply connector 41, ensuring an accurate transmission of the adapter type information. As shown in FIG. 4, the endoscope connectors 22 of the adapter 2 are connected to the endoscope ports 10 of the endoscope 6.

Figure 5:
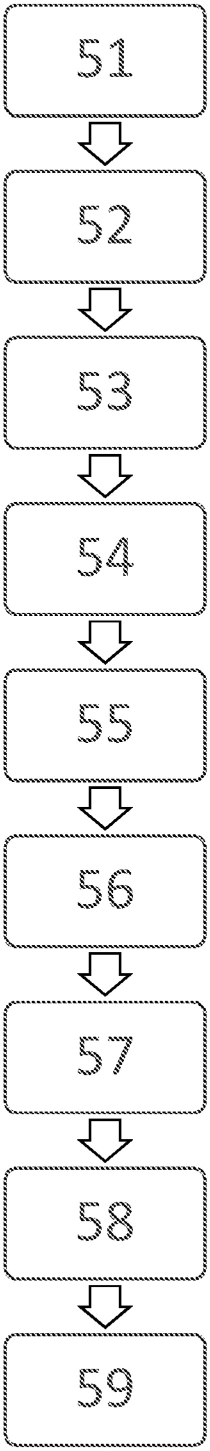
FIG. 5 illustrates a schematic flow chart of a method of connecting an adapter to an air supply connector of a storage cabinet, and FIG. 6 a schematic flow chart of a method for disconnecting an adapter from an air supply connector of a storage cabinet.

FIG. 5 schematically depicts a flow chart of a method for connecting an adapter 2 to an air supply connector 41 of the storage cabinet 4. In step 51 of the method, a user RFID tag is scanned with the RFID receiver 44, 45. If the user RFID tag is identified as belonging to an authorized user, the doors 48 are unlocked in step 52. In step 53, the RFID tag 26 of the adapter 2 is scanned by the RFID receivers 44, 45 in order to transmit the adapter type information to the storage cabinet 4. In step 54, the air inlet connector 20 of the adapter 2 is connected to a free air supply connector 41. The air valve 42 is configured to automatically open, when this connection is made, which comprises step 55. In step 56, a pressurized airflow is generated by the opening of the air valve 42, the pressurized airflow being directed from the air supply 40 through the air supply connector 41, the air inlet connector 20, the tube 24 and the endoscope connector 22 of the adapter 2 to the endoscope 6. In step 57, the control device 43 detects the pressurized airflow, for example with a flow sensor arranged inside the air supply connector 41. Through the detection of the airflow, the control device learns which air supply connector 41 has been connected to the adapter 2. Through the adapter type information, the control device 43 also learns what type of adapter 2 has been connected to this air supply connector 41. This comprises step 58. In step 59, the control device 43 controls the air supply 40 to adapt for example the flow parameters for the air supply connector 41 to the specifications of the adapter type information.

Further parameters can be taken into account. According to further embodiments, the adapter type information can comprises one or more of a plurality of parameter(s) selected from the following list:

a connection time for a user to connect the endoscope adapter and the storage cabinet, a minimum and/or a maximum valve opening position of the air valve in at least one of the air supply connectors of the storage cabinet, wherein the air supply connector comprises the air valve, which is configured to control the pressurized air flow through the air supply connector, such as during a main drying phase, a minimum and/or a maximum pressure of the pressurized air flow through the air supply connector, such as during a main drying phase, a duration of a pre-drying phase, an airflow and/or an airflow pulse length during a pre-drying phase, a duration of a storage phase, an airflow and/or a pulse length during a storage phase.

For example, the control device (43) can set the timers for the pre-drying phase and the main drying phase (for example several minutes for pre-drying and one or two hours for main drying) and the storage phase (for example one week or four weeks).

This method for connecting the adapter 2 to the air supply connector 41 is only an exemplary embodiment. Other embodiments of the method may comprise additional steps, fewer steps or different steps or the order of steps may be changed. For example, steps 51 and 52 may be omitted and/or step 53 may be performed after step 57 or 58.

Figure 6:
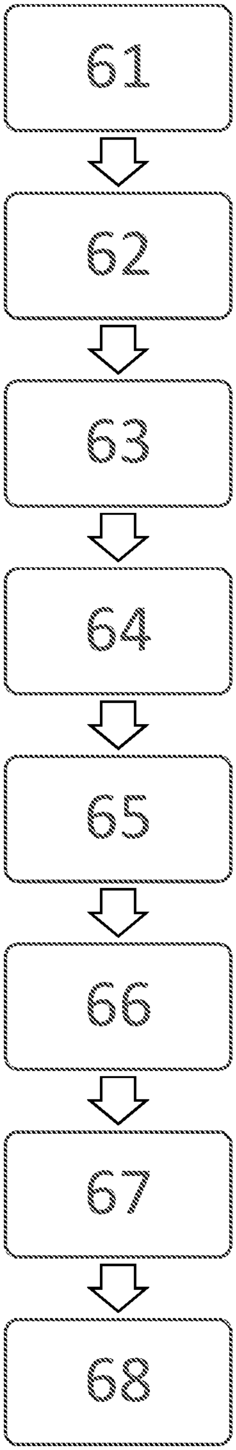

FIG. 6 shows an exemplary embodiment of a flow chart for a method for disconnecting an adapter 2 from an air supply connector 41 of a storage cabinet 4. According to step 61, the user RFID tag is scanned by the RFID receiver 44, 45 and the doors unlocked in step 62, if the user RFID tag is identified as belonging to an authorized user. In step 63, the adapter 2 is removed by disconnecting the air inlet connector 20 from the air supply connector 41 and the endoscope connectors 22 from the endoscope ports 10 of the endoscope 6. Disconnecting the air inlet connector 20 from the air supply connector 41 results in the closing of the air valve 42 in step 64. In step 65, because the air valve 42 is closed, no pressurized airflow is going through the air supply connector 41 and the adapter 2. The control device 43 can detect the missing airflow in step 66. By detecting the missing airflow, the control device 43 can learn which adapter 2 has been disconnected from which air supply connector 41 in step 67. Then, in step 68, the control device 43 controls the air supply 40 to reset the flow parameters for this air supply connector 41 to a standard value. The control device 43 can also trigger the end of the pre-drying, main drying or the storage phase, which is subsequently documented by the cabinet.

Just like the method for connecting an adapter, the method for disconnecting an adapter shown in FIG. 6 may also comprise more steps, less steps, different steps or the order of steps may be changed.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES

1 endoscope storage system
2 adapter
4 storage cabinet
6 endoscope
10 endoscope port
20 air inlet connector
22 endoscope connector
24 tube
26 RFID tag
40 air supply
41 air supply connector
42 air valve
43 control device
44 RFID receiver
45 RFID receiver
46 hull
47 control panel
48 door
49 holder
51 to 59 method steps
61 to 68 method steps

What is claimed is:

1. An adapter comprising:

an air inlet connector configured to be removably connected to an air supply connector of a storage cabinet;

at least one endoscope connector configured to be connected to an endoscope port of an endoscope; and at least one tube connecting the air inlet connector and the at least one endoscope connector, wherein the air inlet connector is configured to connect the adapter to the air supply connector and to disconnect the adapter from the air supply connector of the storage cabinet, the adapter comprises an RFID tag, the RFID tag being configured to store adapter type information about an adapter type of the adapter, and the RFID tag is configured to send the adapter type information to an RFID receiver of the storage cabinet.

2. The adapter according to claim 1, wherein the RFID tag is arranged on or inside the air inlet connector.

3. The adapter according to claim 1, wherein the adapter type information comprises flow parameters, the flow parameters specifying one or more of an air pressure value and a flow rate value of a pressurized air flow to be guided through the adapter.

4. A storage cabinet comprising:

an air supply;

at least two air supply connectors connected to the air supply;

at least one RFID receiver; and a controller comprising hardware;

wherein the at least two air supply connectors are configured to be connected to the air inlet connector of the adapter according to claim 1;

the air supply is configured to apply an air pressure to the air supply connectors;

the air supply connectors each comprise an air valve;

the air valve in each air supply connector of the at least two air supply connectors is configured to be mechanically opened when a connection is established between the air inlet connector of the adapter and a corresponding one of the at least two air supply connectors comprising the opened air valve;

the opened air valve causes a pressurized air flow through the corresponding one of the at least two air supply connectors;

the controller is configured to detect the pressurized air flow in order to detect which air supply connector of the at least two air supply connectors has been connected to the air inlet connector;

the at least one RFID receiver is configured to receive the adapter type information from the RFID tag of the adapter and to transmit the adapter type information to the controller; and the controller is configured to adapt flow parameters of the pressurized air flow based on the adapter type information.

5. The storage cabinet according to claim 4, wherein the at least one RFID receiver comprising at least two RFID receivers, wherein one of the at least two RFID receivers is arranged on or inside each of the at least two air supply connectors.

6. The storage cabinet according to claim 5, wherein the at least two RFID receiver is arranged as part of a control panel of the storage cabinet.

7. The storage cabinet according to claim 4, wherein the at least one RFID receiver is arranged on or outside a hull of the storage cabinet.

8. The storage cabinet according to claim 4, wherein the controller is configured to adapt flow parameters of the pressurized air flow of each of the at least two air supply connectors only after the connection of one of the at least two air supply connectors to the air inlet connector has been detected.

9. The storage cabinet according to claim 4, wherein the controller is configured to measure a connection time for which the adapter is connected to one of the at least two air supply connectors, compare the connection time with a predefined lifetime of the adapter and generate a warning when the connection time exceeds the lifetime.

10. An endoscope storage system, comprising the storage cabinet according to claim 4.

11. A method for connecting an adapter to one of at least two air supply connectors of a storage cabinet, the method comprising:

transmitting adapter type information from a RFID tag of the adapter to a RFID receiver of the storage cabinet;

removably connecting an air inlet connector of the adapter to a first air supply connector of at least two air supply connectors, wherein an air pressure is applied to each of the at least two air supply connectors with an air supply of the storage cabinet, an air valve in the first air supply connector is opened by connecting the air inlet connector to the first air supply connector, and the opening of the air valve causes a pressurized air flow through the first air supply connector to the adapter;

detecting, with a controller of the storage cabinet, which of the at least two air supply connectors has been connected with the air inlet connector by detecting the pressurized air flow;

sending the adapter type information from the RFID receiver to the controller; and adapting flow parameters of the pressurized air flow based on the adapter type information.

12. The method according to claim 11, wherein the adapting of the flow parameters is performed after the detecting which of the at least two air supply connectors has been connected with the air inlet connector.

13. The method according to claim 11, further comprising:

measuring a connection time, for which the adapter is connected to one of the at least two air supply connectors, wherein the connection time is compared with a predefined lifetime of the adapter, and a warning is generated when the connection time exceeds the lifetime.

14. A method for disconnecting an adapter from a first air supply connector of at least two air supply connectors of a storage cabinet, the method comprising:

disconnecting an air inlet connector of the adapter from a the first air supply connector, wherein an air valve in the first air supply connector is closed by disconnecting the air inlet connector from the first air supply connector, and the closing of the air valve causes a pressurized air flow through the first air supply connector to stop;

detecting, with a controller of the storage cabinet, which of the at least two air supply connectors has been disconnected from the air inlet connector by detecting the termination of the pressurized air flow; and setting flow parameters for an air pressure applied to the first air supply connector back to a predefined value.

* * * * *